(12) United States Patent
Hasegawa

(10) Patent No.: US 11,660,421 B2
(45) Date of Patent: May 30, 2023

(54) MEDICAL MANIPULATOR AND MEDICAL DEVICE

(71) Applicant: OLYMPUS CORPORATION, Tokyo (JP)

(72) Inventor: Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 410 days.

(21) Appl. No.: 16/684,646

(22) Filed: Nov. 15, 2019

(65) Prior Publication Data

US 2020/0078557 A1 Mar. 12, 2020

Related U.S. Application Data

(63) Continuation of application No. PCT/JP2017/019266, filed on May 23, 2017.

(51) Int. Cl.
*A61M 25/00* (2006.01)
*A61M 25/01* (2006.01)
(Continued)

(52) U.S. Cl.
CPC ...... *A61M 25/0082* (2013.01); *A61M 25/003* (2013.01); *A61B 17/00234* (2013.01);
(Continued)

(58) Field of Classification Search
CPC ............ A61M 25/0082; A61M 25/003; A61M 2025/0039; A61M 2025/017;
(Continued)

(56) References Cited

U.S. PATENT DOCUMENTS

2004/0019352 A1 1/2004 Kidooka
2009/0023989 A1 1/2009 Honda et al.
(Continued)

FOREIGN PATENT DOCUMENTS

EP 1987789 A1 11/2008
JP 4420593 B2 2/2010
(Continued)

OTHER PUBLICATIONS

International Search Report dated Aug. 8, 2017 issued in PCT/JP2017/019266.

*Primary Examiner* — Brooke Labranche
(74) *Attorney, Agent, or Firm* — Scully, Scott, Murphy & Presser, P.C.

(57) ABSTRACT

A medical manipulator includes: an end effector provided at a distal side of the medical manipulator; a proximal housing provided at a proximal side of the medical manipulator; and an elongated portion coupled to both the end effector and the proximal end. The elongated portion includes: a first elongated member coupled to both the end effector and the proximal housing; a second elongated member coupled to only either one of the end effector and the proximal housing, the second elongated member being configured to form by surrounding the first elongated member; and to be slidable in a longitudinal direction relative to the first elongated member; and a third elongated member coupled to both the end effector and the proximal housing, the third elongated member being configured to form an exterior of the elongated portion by surrounding the second elongated member.

20 Claims, 3 Drawing Sheets

(51) Int. Cl.
  *A61B 17/00* (2006.01)
  *A61B 17/29* (2006.01)
(52) U.S. Cl.
  CPC ....... *A61B 17/29* (2013.01); *A61B 2017/2902* (2013.01); *A61B 2017/2932* (2013.01); *A61M 2025/0039* (2013.01); *A61M 2025/0175* (2013.01)
(58) Field of Classification Search
  CPC .... A61M 2025/0036; A61M 2025/004; A61M 25/0032; A61B 17/00234; A61B 17/29; A61B 2017/2902; A61B 2017/2932; A61B 2017/00305; A61B 2017/2905; A61B 34/30
  See application file for complete search history.

(56) References Cited

U.S. PATENT DOCUMENTS

2014/0276593 A1* 9/2014 Nagale .............. A61M 25/0074
                                                    604/506
2016/0287346 A1  10/2016 Hyodo et al.
2017/0020616 A1*  1/2017 Vale ........................ A61B 34/30
2019/0231457 A1   8/2019 Vale et al.

FOREIGN PATENT DOCUMENTS

| JP | 2015-231496 A | 12/2015 |
| JP | 2016-187558 A | 11/2016 |
| WO | WO 2007/096951 A1 | 8/2007 |
| WO | WO 2012/054829 A2 | 4/2012 |
| WO | WO 2015/153111 A1 | 10/2015 |

* cited by examiner

US 11,660,421 B2

MEDICAL MANIPULATOR AND MEDICAL DEVICE

CROSS-REFERENCE TO RELATED APPLICATIONS

This is a continuation of International Application PCT/JP2017/019266, with an international filing date of May 23, 2017, which is hereby incorporated by reference herein in its entirety.

TECHNICAL FIELD

The present invention relates to medical flexible tubes and medical flexible manipulators.

BACKGROUND ART

A known flexible manipulator includes a movable section at the distal end of a long and flexible insertion section and drives the movable section by using wires extending longitudinally through the insertion section (e.g., see Patent Literature 1).

The flexible manipulator according to Patent Literature 1 employs a plastic multi-lumen tube as the insertion section and thus has the wires accommodated in lumens that are separated from each other, so as to eliminate the need for insulating coatings and coil sheaths, thereby achieving cost reduction.

CITATION LIST

Patent Literature

{PTL 1}
The Publication of Japanese Patent No. 4420593

SUMMARY OF INVENTION

An aspect of the present invention is directed to a medical manipulator including: an end effector provided at a distal side of the medical manipulator; a proximal housing provided at a proximal side of the medical manipulator; and an elongated portion coupled to both the end effector and the proximal end, the elongated portion including: a first elongated member coupled to both the end effector and the proximal housing; a second elongated member coupled to only either one of the end effector and the proximal housing, the second elongated member being configured: to form by surrounding the first elongated member; and to be slidable in a longitudinal direction relative to the first elongated member; and a third elongated member coupled to both the end effector and the proximal housing, the third elongated member being configured to form an exterior of the elongated portion by surrounding the second elongated member.

Another aspect of the present invention is directed to a medical device including: an elongeted portion including a proximal end; and an end effector coupled to the elongeted portion; wherein the elongeted portion includes: a guide channel located between a first elongated member and a second elongated member, the guide channel being configured to extend in a longitudinal direction of the elongeted portion; and a wire configured to extend through the guide channel, the wire being mechanically coupled to the end effector, wherein the first elongated member is coupled to both the end effector and the proximal end, and the second elongated member is coupled to only either one of the end effector and the proximal end.

DESCRIPTION OF EMBODIMENTS

A medical flexible tube 2 and a medical flexible manipulator 1 according to an embodiment of the present invention will be described below with reference to the drawings.

Figure 1:
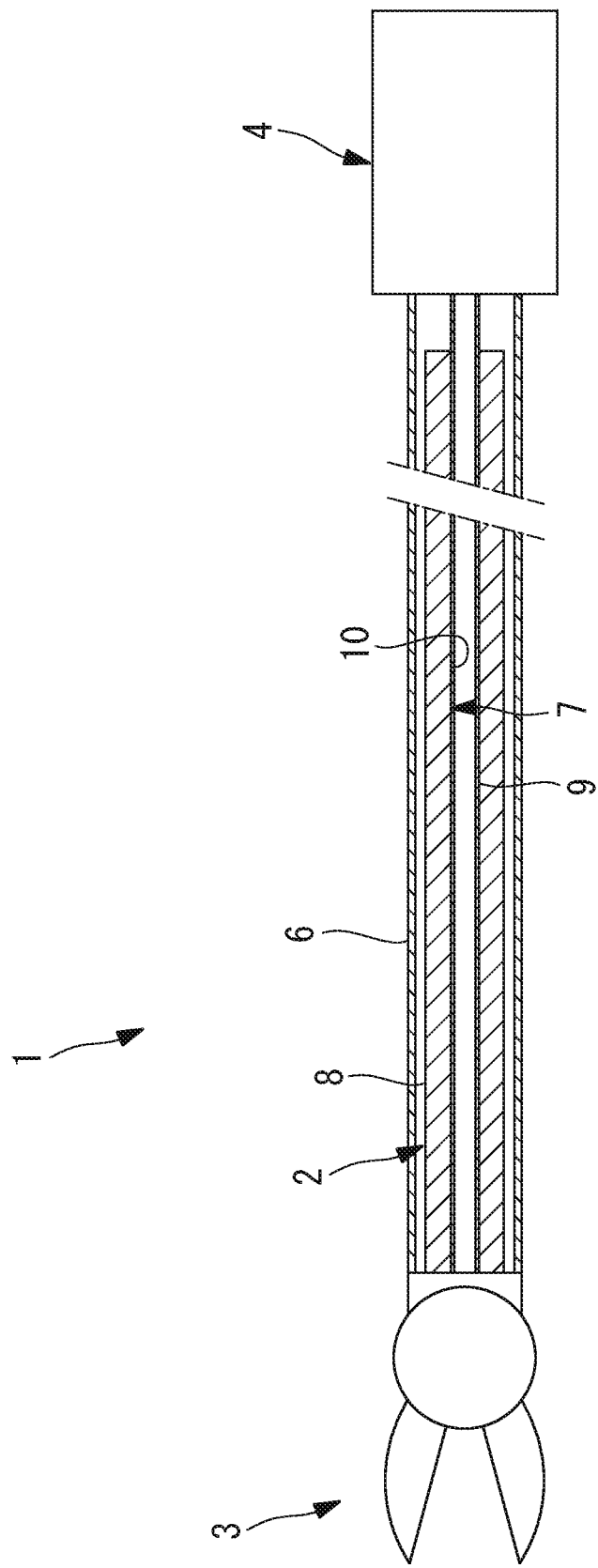
FIG. 1 is a vertical sectional view illustrating a medical flexible manipulator according to an embodiment of the present invention.

As shown in FIG. 1, the medical flexible manipulator 1 according to this embodiment includes a long medical flexible tube 2 according to this embodiment having flexibility, a movable section 3 attached to the distal end of the medical flexible tube 2, a driver 4 that is attached to the proximal end of the medical flexible tube 2 and that generates a motive force, a plurality of wires (motive-force transmission members) 5 that transmit the motive force generated by the driver 4 to the movable section 3, and a tubular outer sheath member 6 whose distal end is attached to the movable section 3 and whose proximal end is attached to the driver 4.

Figure 2:
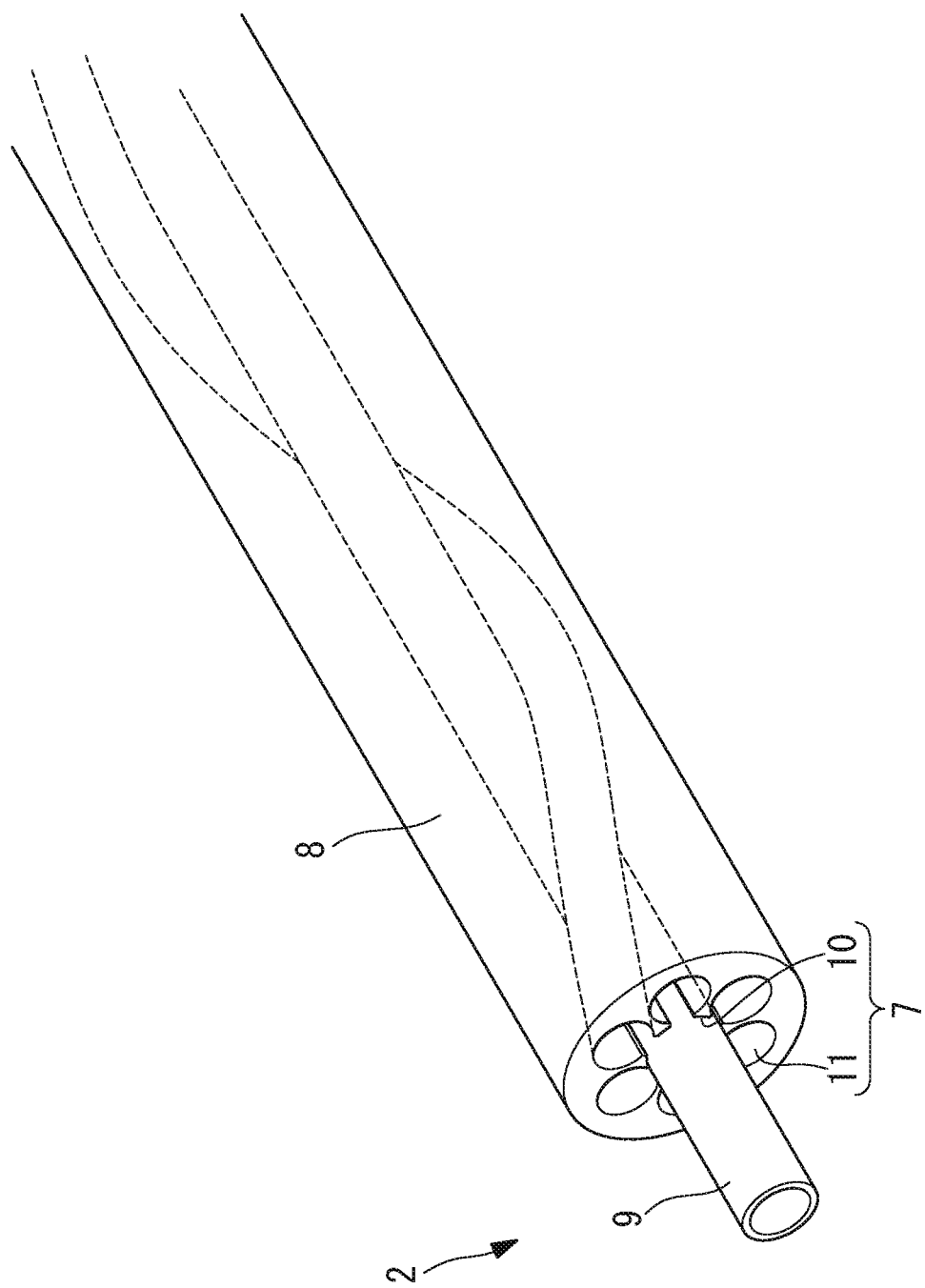
FIG. 2 is a perspective view illustrating an example of a medical flexible tube according to an embodiment of the present invention included in the medical flexible manipulator in FIG. 1.

As shown in FIG. 2, the medical flexible tube 2 according to this embodiment includes a long tube body 8 having a single lumen 7, and also includes a long core 9 fitted in the lumen 7 of the tube body 8.

The tube body 8 is composed of a material having flexibility in the bending direction. For example, an elastic material, such as rubber, is used.

Figure 3:
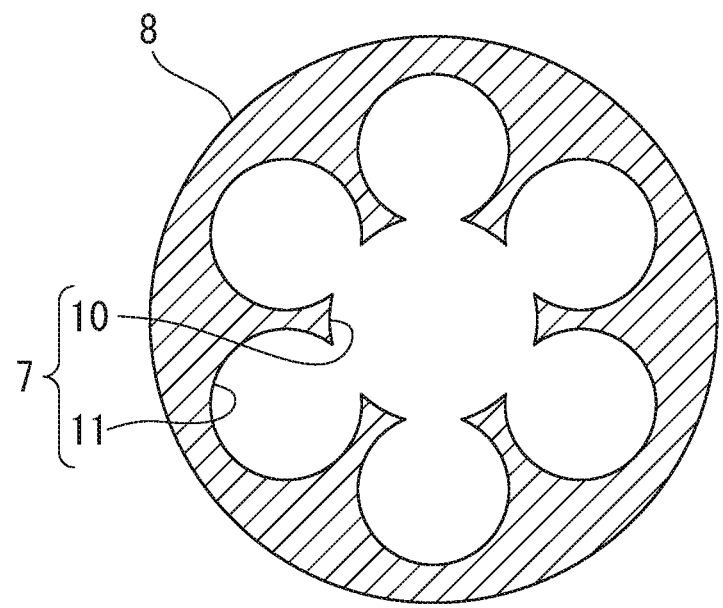
FIG. 3 is a cross-sectional view illustrating a tube body included in the medical flexible tube in FIG. 2.

As shown in FIG. 3, the lumen 7 includes a cross-sectionally-circular center hole 10 disposed at the center of the cross section of the tube body 8, and also includes a plurality of cross-sectionally-circular peripheral holes 11 disposed adjacent to the outer side of the center hole 10 in the radial direction thereof and arranged at intervals in the circumferential direction. The single lumen 7 has a cross-sectional shape in which the center hole 10 and the peripheral holes 11 communicate with each other in the radial direction and in which the plurality of peripheral holes 11 are arranged in a radial pattern at the outer side of the center hole 10 in the radial direction.

As shown in FIG. 3, in this embodiment, the center distance between the center hole 10 and each peripheral hole 11 is set to be smaller than or equal to the sum of the radius of the center hole 10 and the radius of the peripheral hole 11. Furthermore, as shown in FIG. 2, each peripheral hole 11 is formed helically to circle around the center hole 10 in one direction at a predetermined pitch in the longitudinal direction. FIG. 2 shows only one of the peripheral holes 11 with dashed lines to simplify the drawing.

The core 9 has flexibility in the bending direction and is composed of a material having a compression stiffness higher than the compression stiffness of the tube body 8 in the longitudinal direction. For example, the core 9 is formed of a tubular member composed of a plastic or metallic material, such as a coil tube.

Figure 4:
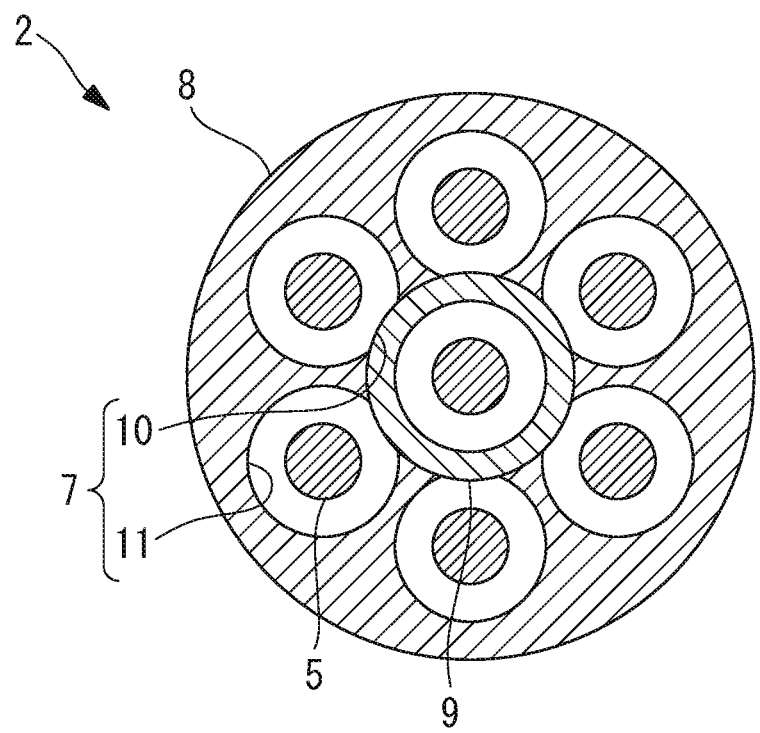
FIG. 4 is a cross-sectional view illustrating the medical flexible tube in FIG. 3.

As shown in FIG. 4, the outer diameter of the core 9 is substantially equal to the inner diameter of the center hole 10 in the lumen 7. Accordingly, by inserting the core 9 into the center hole 10, the outer surface of the core 9 is brought into close contact with the inner surface of the center hole 10 so that the core 9 and the center hole 10 are engaged with each other, whereby the space in the center hole 10 is separated in the radial direction from the spaces in the surrounding peripheral holes 11.

Specifically, with regard to the medical flexible tube 2 according to this embodiment, the core 9 is fitted into the center hole 10 in the tube body 8 so that the tube body 8 itself can be manufactured as a tube having the single lumen 7. After the core 9 is fitted into the center hole 10, it is possible to form a substantially twisted multi-lumen tube having the center hole 10 and the plurality of peripheral holes 11, which are arranged helically in one direction around the center hole 10, independently of each other.

As shown in FIG. 1, in this embodiment, the movable section 3 and the medical flexible tube 2 are fixed to the distal end of the core 9, the driver 4 is fixed to the proximal end of the core 9, and the plurality of wires 5 extend through the peripheral holes 11 and the center hole 10 to connect with the driver 4 and the movable section 3. The proximal end of the tube body 8 and the driver 4 are arranged with a gap therebetween in the longitudinal direction.

The operation of the medical flexible tube 2 and the medical flexible manipulator 1 according to this embodiment having the above-described configuration will be described below.

As mentioned above, the medical flexible tube 2 according to this embodiment is formed by fitting the core 9 into the center hole 10 in the tube body 8 having the single lumen 7. Therefore, it is not necessary to manufacture a multi-lumen tube having many independent lumens as the tube body 8. This is advantageous in that an elongated tube body 8 can be easily manufactured by extrusion molding.

The tubular wall of the tubular core 9 fitted in the center hole 10 separates the peripheral holes 11 from each other and the peripheral holes 11 and the center hole 10 from each other as independent lumens. Therefore, when the tube body 8 is to be manufactured, it is not necessary to form a wall having a required thickness between the peripheral holes 11 and the center hole 10, and the peripheral holes 11 and the center hole 10 can be disposed as close to each other as possible. This is advantageous in that the tube body 8 can have a sufficiently small diameter.

When the medical flexible manipulator 1 according to this embodiment is to be inserted into a curvy body cavity, the medical flexible tube 2 is bent. Since the peripheral holes 11 through which the wires 5 extend are helical, it is possible to suppress a difference in path lengths between the peripheral holes 11 caused by the bending.

Furthermore, because the core 9 fitted in the center hole (sometimes referred to as "lumen" hereinafter) 10 has a sufficient compression stiffness, the distance between the movable section 3 and the driver 4 is maintained without changing even when the medical flexible tube 2 is bent. A compressive force acts on the tube body 8 in the longitudinal direction at the inner side of the bend, whereas a tensile force acts on the tube body 8 in the longitudinal direction at the outer side of the bend. However, since the tube body 8 is separated from the driver 4 by a gap, the gap is increased and decreased to balance out the compressive force and the tensile force, causing the tube body 8 to move in the longitudinal direction relative to the core 9. Consequently, the tube body 8 is prevented from being excessively compressed or pulled, which is advantageous in that the tube body 8 can be maintained in a sound state.

Moreover, because the tube body 8 having the helical peripheral holes (sometimes referred to as "lumens" hereinafter) 11 is prevented from being excessively compressed or pulled, the pitch of the helix is prevented from changing significantly, which is advantageous in that variations in the path lengths of the wires 5 can be suppressed.

Specifically, in the medical flexible manipulator 1 according to this embodiment, the motive force generated as a result of actuation of the driver 4 is transmitted to the movable section 3 by the plurality of wires 5 fitted in the plurality of lumens 10 and 11 formed in the medical flexible tube 2. When the movable section 3 is to be moved in accordance with the tension of the wires 5, variations in the path lengths between the lumens 10 and 11 caused by the bending of the medical flexible tube 2 can be minimized, and any of the wires 5 is prevented from stretching or loosening. This is advantageous in that the controllability of the movable section 3 can be improved.

As an alternative to this embodiment in which the medical flexible tube 2 has the helical peripheral holes 11, the peripheral holes 11 may be straight. Even in such a case, it is possible to achieve the similar advantage of the improved ease of manufacture of the tube body 8 having the single lumen 7.

As an alternative to this embodiment in which the tubular core 9 is fitted into the center hole 10 to make the peripheral holes 11 independent of each other, the core 9 may be a solid core.

Furthermore, as an alternative to this embodiment in which the tube body 8 and the driver 4 have a gap therebetween, the tube body 8 and the driver 4 may be connected to each other, and the tube body 8 and the movable section 3 may have a gap therebetween. As another alternative, the tube body 8 may be separated from both the driver 4 and the movable section 3 by gaps.

An aspect of the present invention is directed to a medical flexible tube including: a long tube body having flexibility and including a single lumen extending therethrough in a longitudinal direction; and a long core having flexibility and fitted into the lumen in the tube body. The lumen includes a center hole disposed at the center of a cross section of the tube body and a plurality of peripheral holes disposed adjacent to an outer side of the center hole in a radial direction and arranged at intervals in a circumferential direction, the peripheral holes communicating with the center hole in the radial direction. The core blocks an opening of each peripheral hole toward the center hole.

According to this aspect, the long and flexible tube body has a single lumen so that extrusion-molding-based manufacture is easier, as compared with a multi-lumen tube. By fitting the long and flexible core into the lumen, the opening of each peripheral hole toward the center hole is blocked by the core, so that a multi-lumen tube having a plurality of substantially independent peripheral holes can be formed.

Furthermore, in the above aspect, the core may be tubular and may be fitted into the center hole to separate the peripheral holes from the center hole in the radial direction.

Accordingly, the center hole and the peripheral holes are separated from each other, so that a multi-lumen tube having a plurality of substantially independent peripheral holes can be formed.

In the above aspect, the center hole and the peripheral holes may each have a cross-sectionally circular shape, and a center distance between the center hole and each peripheral hole in the radial direction may be smaller than or equal to a sum of a radius of the center hole and a radius of the peripheral hole.

Accordingly, the center distance between the center hole and each peripheral hole that communicate with each other is decreased, so that the tube body can be made narrower.

Furthermore, in the above aspect, each peripheral hole may be disposed helically around the center hole in the longitudinal direction.

Accordingly, a difference in path lengths between the peripheral holes can be prevented when the tube body is bent.

Another aspect of the present invention is directed to a medical flexible manipulator including: the medical flexible tube according to the above aspect; a movable section attached to a distal end of the core; a driver that is attached to a proximal end of the core and that generates a motive force; and a plurality of elongated motive-force transmission members that are respectively fitted into the peripheral holes and that transmit the motive force generated by the driver to the movable section. A compression stiffness of the core in the longitudinal direction is higher than a compression stiffness of the tube body in the longitudinal direction. The tube body and the core are disposed in a relatively movable manner in the longitudinal direction. The tube body is separated from at least one of the movable section and the driver by a gap.

According to this aspect, the motive force generated as a result of actuation of the driver is transmitted to the movable section by the motive-force transmission members, and an affected site can be treated by moving the movable section. In this case, when the medical flexible tube is bent, the entire length of the tube body is maintained by the core having a high compression stiffness. On the other hand, a compressive force acts on the tube body in the longitudinal direction at the inner side of the bend, whereas a tensile force acts on the tube body in the longitudinal direction at the outer side of the bend.

Because the tube body is disposed in a movable manner in the longitudinal direction relative to the core and is separated from at least one of the movable section and the driver by a gap, the compressive force and the tensile force acting on the tube body cause the tube body to move relative to the core. Consequently, the tube body is prevented from receiving an excessive compressive force or tensile force, so that the tube body can be maintained in a sound state.

Furthermore, since the tube body is prevented from being excessively compressed or pulled, it is possible to suppress variations in the path lengths of the peripheral holes accommodating the motive-force transmission members. Consequently, the controllability of the movable section can be prevented from deteriorating due to bending of the medical flexible tube.

The present invention is advantageous in that it achieves easier extrusion-molding-based manufacture.

REFERENCE SIGNS LIST 1 medical flexible manipulator
2 medical flexible tube (elongated portion)
3 movable section (end effector)
4 driver (actuator)
5 wire (motive-force transmission member)
6 tubular outer sheath member (third elongated member)
7 lumen
8 tube body (second elongated member)
9 core (first elongated member, first lumen)
10 center hole
11 peripheral hole (second lumen)

The invention claimed is:

1. A medical manipulator comprising:
an inner elongated tube;
an end effector connected at a distal side of the inner elongated tube;
a proximal housing connected at a proximal side of the inner elongated tube, the inner elongated tube being fixed to the end effector and to the proximal housing; and
an outer elongated tube having a second distal end and a second proximal end the outer elongated tube being formed to circumferentially surround the inner elongated tube such that only the second distal end is fixed to the end effector and the second proximal end is free to move longitudinally relative to the inner elongated tube or only the second proximal end is fixed to the proximal housing and the second distal end is free to move longitudinally relative to the inner elongated tube.

2. The medical manipulator according to claim 1, wherein the outer elongated tube has a first compression stiffness lower than a second compression stiffness of the inner elongated tube.

3. The medical manipulator according to claim 1, wherein the outer elongated tube has one or more lumens and the inner and outer elongated tubes are configured to together define the one or more lumens extending therethrough in a longitudinal direction.

4. The medical manipulator according to claim 3, wherein:
the one or more lumens are partially defined by an outer surface of the inner elongated tube and partially defined by an inner surface of the outer elongated tube; and
an additional lumen is defined by an inner surface of the inner elongated tube.

5. The medical manipulator according to claim 4, wherein the additional lumen is configured to extend longitudinally within the inner elongated tube; and
the one or more lumens are configured to helically extend around the additional lumen in the longitudinal direction.

6. The medical manipulator according to claim 4, further comprising:
an operation wire coupled to both the proximal housing and the end effector, the operation wire being inserted into one of the one or more lumens and into the additional lumen,
wherein the operation wire is configured to operate the end effector.

7. The medical manipulator according to claim 4, wherein the outer surface of the inner elongated tube is not fixed relative to the inner surface of the outer elongated tube.

8. The medical manipulator according to claim 1, wherein only the second distal end of the outer elongated tube is fixed to the end effector; and
the second proximal end is free to move longitudinally relative to the inner elongated tube.

9. The medical manipulator according to claim 1, wherein one of the second distal end and the second proximal end of the outer elongated tube is configured not to move relative to the inner elongated tube when the inner and outer elongated tubes are bent; and an other of the second distal end and the second proximal end of the outer elongated tube is configured to move longitudinally relative to the inner elongated tube when the inner and outer elongated tubes are bent.

10. The medical manipulator according to claim 1, further comprising an outer sheath connected at a third distal end to the end effector and at a third proximal end to the proximal housing, the outer sheath being configured to surround the outer elongated tube.

11. The medical manipulator according to claim 1, wherein
the inner elongated tube has a first longitudinal length; and
the outer elongated tube has a second longitudinal length less than the first longitudinal length.

12. A medical device comprising:
a flexible outer sheath;
an end effector coupled to a distal end of the outer sheath;
a first elongated tube having a first distal end connected to the end effector and extending longitudinally along an inside of the outer sheath; and
a second elongated tube disposed between the first elongated tube and the outer sheath, and only a second distal end of the second elongated tube is fixed to the end effector and a second proximal end of the second elongated tube is free to move longitudinally relative to the first elongated tube.

13. The medical device according to claim 12, wherein:
the second elongated tube has one or more lumens;
the first elongated tube has an additional lumen configured to extend longitudinally within the first elongated tube; and
the one or more lumens are configured to helically extend around the additional lumen.

14. The medical device according to claim 13, wherein
the one or more lumens are partially defined by an outer surface of the first elongated tube and are partially defined by an inner surface of the second elongated tube; and
the additional lumen is defined by an inner surface of the first elongated tube.

15. The medical device according to claim 14, wherein the outer surface of the inner elongated tube is not fixed relative to the inner surface of the outer elongated tube.

16. The medical device according to claim 14, wherein one or more of the one or more lumens and the additional lumen are configured to carry an operation wire.

17. The medical manipulator according to claim 12, wherein the second elongated tube has a first compression stiffness lower than a second compression stiffness of the first elongated tube.

18. The medical device according to claim 12, wherein the second proximal end of the second elongated tube is configured to move longitudinally relative to the first elongated tube and the outer sheath when the outer sheath, the first elongated tube and the second elongated tube are bent.

19. The medical device according to claim 12, wherein a first longitudinal length of the first elongated tube is longer than a second longitudinal length of the second elongated tube.

20. A medical manipulator comprising:
an inner elongated tube;
an end effector connected at a distal side of the inner elongated tube;
a proximal housing connected at a proximal side of the inner elongated tube, the inner elongated tube being fixed to the end effector and to the proximal housing; and
an outer elongated tube having a second distal end and a second proximal end, the outer elongated tube being formed to circumferentially surround the inner elongated tube such that only one of the second distal end is fixed to the end effector or only the second proximal end is fixed to the proximal housing;
wherein the outer elongated tube has one or more lumens and the inner and outer elongated tubes are configured to together define the one or more lumens extending therethrough in a longitudinal direction;
the one or more lumens are partially defined by an outer surface of the inner elongated tube and partially defined by an inner surface of the outer elongated tube; and
an additional lumen is defined by an inner surface of the inner elongated tube.

* * * * *